United States Patent [19]
Borton et al.

[11] Patent Number: 5,078,497
[45] Date of Patent: Jan. 7, 1992

[54] DENSITOMETER FOR A LIQUID DEVELOPER MATERIAL

[75] Inventors: Michael D. Borton, Ontario; Fred F. Hubble, III, Rochester; James P. Martin, Rochester; Theresa K. Mattioli, Rochester; Ralph A. Shoemaker, Rochester, all of N.Y.

[73] Assignee: Xerox Corporation, Stamford, Conn.

[21] Appl. No.: 399,051

[22] Filed: Aug. 25, 1989

[51] Int. Cl.$^5$ ............................................. G01N 21/47
[52] U.S. Cl. ..................................... 356/446; 356/445
[58] Field of Search ............... 356/445, 446, 389, 448, 356/447

[56] References Cited

U.S. PATENT DOCUMENTS

| | | | |
|---|---|---|---|
| 2,315,282 | 3/1943 | Snow | 356/446 |
| 3,994,723 | 11/1976 | Brooke | 356/389 |
| 4,226,541 | 10/1980 | Tisue | 356/446 |
| 4,553,033 | 11/1985 | Hubber, III et al. | 250/353 |
| 4,565,450 | 1/1986 | Wirz et al. | 356/446 |
| 4,582,774 | 4/1986 | Landa | 430/126 |
| 4,677,298 | 6/1987 | Zelmanovic et al. | 356/446 |
| 4,737,035 | 4/1988 | Aoki et al. | 356/446 |
| 4,787,238 | 11/1988 | Seki et al. | 356/446 |
| 4,796,065 | 1/1989 | Kanbayashi | 355/14 E |
| 4,799,082 | 1/1989 | Suzuki | 355/14 R |
| 4,806,002 | 2/1989 | Simeth et al. | 356/445 |
| 4,989,985 | 2/1991 | Hubble, III et al. | 356/446 |

*Primary Examiner*—Davis L. Willis
*Assistant Examiner*—Hoa Pham
*Attorney, Agent, or Firm*—H. Fleischer; J. E. Beck; R. Zibelli

[57] ABSTRACT

A densitometer which measures the reduction in the specular component of the reflectivity of a portion of a surface having a liquid deposited thereon. Collimated light rays, in the visible spectrum, are projected onto the portion of the surface having the liquid thereon. The light rays reflected from the portion of the surface having the liquid deposited thereon are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

18 Claims, 6 Drawing Sheets

DENSITOMETER FOR A LIQUID DEVELOPER MATERIAL

This invention relates generally to a printing system in which a liquid image is transferred to a copy sheet, and more particularly concerns an improved densitometer for use therein to detect a reduction in the specular reflectivity of a surface having a liquid deposited thereon.

There are different printing processes which employ a moving master for transferring an image to a sheet of paper. One such technique is used to produce multiple color proof copies from halftone film separations. Initially, an electrostatic master is exposed to a halftone film separation. This forms a photochemical latent image on the master corresponding to the halftone film separation. Four masters are made. One of the masters corresponds to black with the other masters corresponding typically to the substractive primary colors of the desired proof copy. The masters are then placed in the printing machine and secured to rotating cylinders. One master is mounted releasably on each cylinder. Each master is charged to a substantially uniform potential. The charge bleeds away except in the image areas to form an electrostatic latent image thereon corresponding to the image areas of the halftone film separation. The latent image is developed by bringing a liquid developer material into contact therewith. The liquid developer material comprises a liquid carrier having pigmented particles dispersed therein. These latent images are developed with developer material having a color corresponding to the subtractive primary color of the corresponding halftone film separation. Thereafter, the differently colored developed images are transferred from the master sheets to the copy sheet in superimposed registration with one another. Heat is then applied to permanently fuse the image to the copy sheet so as to form a color proof copy.

The printing system uses a different liquid developer unit for each master. As successive copies are made, the liquid developer material is depleted from the developer unit. Depletion of the liquid developer material causes the density of the liquid image to decrease. Clearly, it is necessary to measure the developability of the liquid developer material to insure that the latent image is being properly developed. This is achieved by a closed loop system which regulates developability. Developability, as it pertains to a printing machine employing liquid developer material, is the ability of the liquid developer material to develop the latent image with at least a minimum specified density. It has long been recognized that a closed loop system, which regulates developability by measuring the density of the developed image, optimizes cost and performance. This is due to the relative stability of the transfer and fusing processes. Also, by modulating one parameter, compensation for other factors contributing to low copy quality can be partially accomplished. The use of densitometers for measuring the optical density of toner particles is well known. However, densitometers used for dry developer materials are generally unsuitable for use with liquid developer materials. The liquid developer material generally uses a liquid carrier whose index of refraction matches that of the polymer binder of the toner particles therein and prevents scattering of light rays from occurring at the surface of the particles. Various types of devices have been used previously. The following disclosures appear to be relevant:

U.S. Pat. No. 4,553,033
Patentee: Hubble, III et al.
Issued: Nov. 12, 1985

U.S. Pat. No. 4,796,065
Patentee: Kanbayashi
Issued: Jan. 3, 1989

U.S. Pat. No. 4,799,082
Patentee: Suzuki
Issued: Jan. 17, 1989

U.S. Pat. No. 4,806,002
Patentee: Simeth et al.
Issued: Feb. 21, 1989

Co-pending U.S. patent application Ser. No. 07/246,242
Applicant: Hubble III et al.
Filed: Sept. 19, 1988

The relevant portions of the foregoing patents may be briefly summarized as follows:

U.S. Pat. No. 4,553,033 discloses an infrared reflectance densitometer including a light emitting diode, a collimating lens through which light is projected to a photosensitive surface, a collector lens and a field lens through which reflected light is focused onto a signal photodiode, and a control photodiode onto which a portion of reflected light is directed to control light output. The mount of light received on the signal photodiode is a measurement of the reflectance from the surface of the photoreceptor which, in turn, is proportional to the density of the toner particles thereon.

U.S. Pat. No. 4,796,065 describes an apparatus for detecting image density in a copier a circuit using a light emitting diode and a pair of phototransistors and a comparator is used to determine image density.

U.S. Pat. No. 4,796,065 discloses a reproducing apparatus having a light emitting diode and a phototransistor to determine whether the transfer paper has separated from the surface of the photoconductive drum. The light emitting diode has a wavelength of 420 nanometers or less, or between 500 and 660 nanometers.

U.S. Pat. No. 4,806,002 describes a densitometer for use in printing presses. Photodiodes, having a mask which acts like a collimator to reduce light reflected onto the photodiode from other than the zone of the printed sheet just below the photodiode, are mounted in a side by side manner. Light emitting diodes illuminate an ink test strip. The photodiodes measure the reflected light from the test strip to determine the the density of the ink.

Co-pending U.S. patent application Ser. No. 07/246,242 describes an infrared densitometer which measures the reduction in the specular component of reflectivity as toner particles are progressively deposited on a moving photoconductive belt. Collimated light rays are projected onto the toner particles. The light rays reflected from at least the toner particles are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays. This type of densitometer is inoperative when used with colored liquid inks containing pigments transmissive to infrared light. This is caused by both the infrared transmissive properties of the visible pigments used in this type of printing process and matching the index of refraction of the transparent liquid in which the pigment containing the toner particles are suspended and the polymer binder of the toner particles in which the pigments are held. It is necessary and advantageous to replace the infrared light sources with with a light source that is more strongly reflected or absorbed by those pigments. Since the pigments are designed to produce visible images, a light source in the visible spectrum is most suitable.

Pursuant to the features of the present invention, there is provided an apparatus for measuring the reduction in the specular reflectance of a surface having a liquid deposited on a portion thereof. The apparatus includes means for projecting light rays, in the visible spectrum, onto the portion of the surface having the liquid thereon. Means are provided for detecting the total reflectivity of the portion of the surface having the liquid deposited thereon and the diffuse component of the total reflectivity of the portion of the surface having the liquid deposited thereon and generating a total signal indicative of the total reflectivity and a diffuse signal indicative of the diffuse component of the total reflectivity. Means, responsive to the difference between the total signal and the diffuse signal, generate a specular signal indicative of the specular component of the total reflectivity.

In accordance with another aspect of the present invention, there is provided a printing machine of the type in which the reduction in specular reflectance of a member having a liquid deposited on a portion thereof is detected. The improvement includes means for projecting light rays, in the visible spectrum, onto the portion of the member having the liquid deposited thereon. Means are provided for detecting the total reflectivity of the portion of the member having the liquid deposited thereon and the diffuse component of the total reflectivity of the portion of the member having the liquid deposited thereon and generating a total signal proportional to the total reflectivity and a diffuse signal proportional to the diffuse component of the total reflectivity of the liquid. Means, responsive to the difference between the total signal and the diffuse signal, generate a specular signal proportional to the specular component of the total reflectivity.

Another aspect of the present invention is a densitometer adapted to measure the reduction in the specular component of the reflectivity of a surface having a liquid deposited on a portion thereof. The densitometer includes a collimating lens. A light source is positioned to project light rays, in the visible spectrum, through the collimating lens onto the portion of the surface having the liquid deposited thereon. A collector lens is positioned to receive the light rays reflected from the portion of the surface having the liquid deposited thereon. A photosensor array is positioned to receive the light rays transmitted through the collector lens and generates a total signal proportional to the total reflectivity of the portion of the surface having the liquid deposited thereon and a diffuse signal proportional to the diffuse component of the total reflectivity of the portion of the surface having the liquid deposited thereon. Control circuitry, electrically connected to the photosensor array, compares the total signal and the diffuse signal to determine the difference therebetween for generating a specular signal proportional to the specular component of the total reflectivity of the surface having the liquid deposited thereon.

Other aspects of the present invention will become apparent as the following description proceeds and upon reference to the drawings, in which.

While the present invention will hereinafter be described in connection with a preferred embodiment thereof, it will be understood that it is not intended to limit the invention to that embodiment. On the contrary, it is intended to cover all alternatives, modifications and equivalents as may be included within the spirit and scope of the invention as defined by the appended claims.

Figure 1:
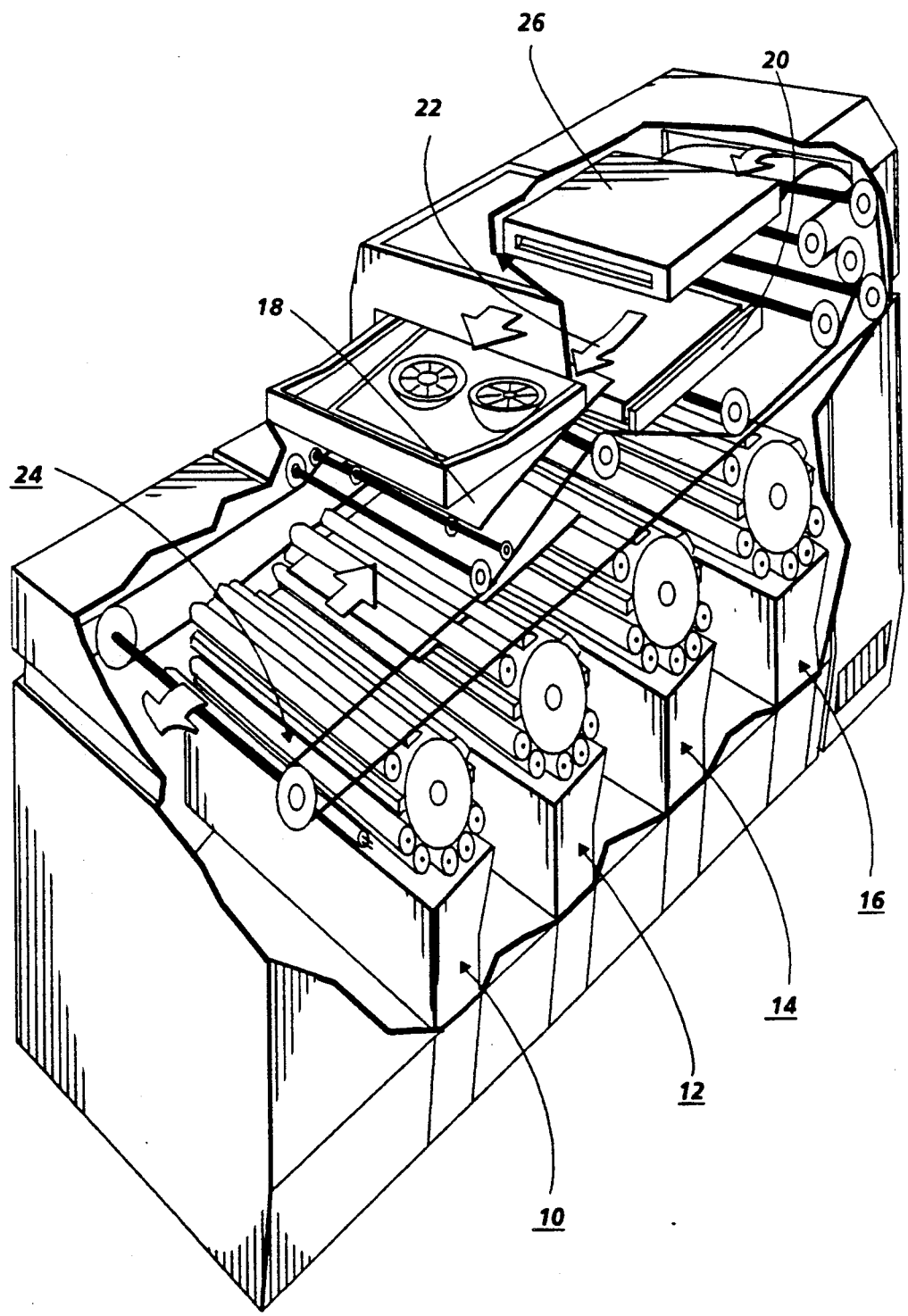
FIG. 1 is a schematic, perspective view showing an illustrative printing machine incorporating the features of the present invention therein.

For a general understanding of the features of the present invention, reference is made to the drawings. In the drawings, like reference numerals have been used throughout to designate identical elements. FIG. 1 schematically depicts the various components of an illustrative printing machine incorporating the densitometer of the present invention therein. It will become evident from the following discussion that the densitometer of the present invention is equally well suited for use in a wide variety of printing machines using liquid development, and is not necessarily limited in its application to the particular printing machine shown herein.

Turning now to FIG. 1, the printing machine employs four printing modules, indicated generally by the reference numerals 10, 12, 14, and 16. Each printing module is substantially identical to one another with the only distinction being the color of the developer material. Printing module 10 employs a yellow liquid developer material, printing module 12 a magenta liquid developer material, printing module 14 a cyan liquid developer material, and printing module 16 a black liquid developer material. In operation, a discrete master sheet is formed for each printing module. This is achieved by exposing the master sheet to a halftone film separation. The halftone film separation is a negative corresponding typically to a subtractive primary color of the desired color proof. This records the desired color proof on the master sheet. The master sheet has a photopolymer layer coated on a metalized base and protected with a thin cover sheet. One skilled in the art will appreciate that any other suitable master sheet may also be employed. A contact exposure is made through the halftone film with a high intensity ultraviolet light. In the image areas, the polymerized area of the master sheet becomes an insulator to electric charge. The unexposed polymer retains its conductive properties. After exposure, the cover sheet is removed from the master sheet. The master sheets are then taken to the printing machine and loaded onto the drum of the appropriate printing module. In addition, each master sheet has a test area recorded thereon. The test area consists generally test patches, about 5 centimeters square located at one edge of the non-image area. After the master sheets are loaded in their respective printing modules, the test area is developed with appropriately colored liquid developer material. The reduction in specular reflectance of the master sheet after the test area has been developed with liquid developer material is measured by the densitometer and circuitry of the present invention.

With continued reference to FIG. 1, after the master sheets are loaded in their respective printing modules, the printing machine is actuated to print the color proof. Upon energization of the printing machine, a sheet of support material 18 is advanced from tray 20. The sheet of support material may be made from any suitable material. Typically, however, it is made from plain paper. A sheet feeder separates and advances the uppermost sheet from a stack of sheets in tray 20. The sheet moves in the direction of arrow 22 to a transport, indicated generally by the reference numeral 24. Preferably, transport 24 includes a pair of parallel, spaced chains entrained about spaced sprockets which advance a gripper in a recirculating path. A servo motor rotates one of the sprockets to advance the chains in the direction of arrow 22. The lead edge of the sheet is secured releasably to the gripper and moves in unison therewith. In this way, transport 24 advances the sheet to successive printing modules. The master sheet, in each printing module, is developed with a different color liquid developer material. The differently colored developed images on each master sheet are transferred to sheet 18 in superimposed registration with one another to form a multicolor image thereon. Inasmuch as the printing modules are substantially identical to one another, only printing module 10 will be described in detail hereinafter with reference to FIG. 2. After all of the developed images have been transferred to sheet 18, transport 24 advances sheet 18 through fuser 26. Fuser 26 radiantly heats the sheet having the liquid images transferred thereto. The fuser supplies sufficient heat to dry and permanently affix the transferred image to sheet 18 forming the desired color proof. After fusing, the completed color proof is advanced to a tray for subsequent removal from the printing machine by the operator.

Figure 2:
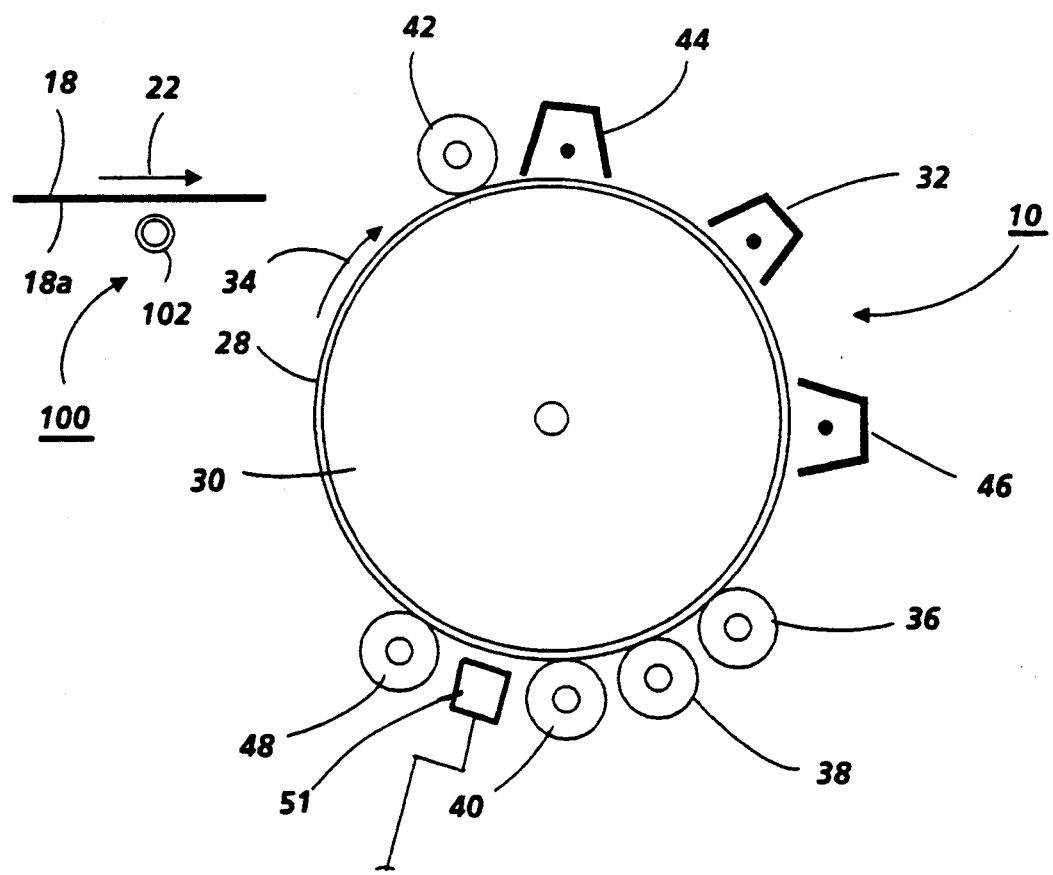
FIG. 2 is a schematic, elevational view depicting one of the printing modules used in the FIG. 1 printing machine.

Turning now to FIG. 2, there is shown further details of printing module 10. As shown thereat, a master sheet 28 is secured releasably to drum 30. During the first cycle, a corona generating device, indicated generally by the reference numeral 32, charges the master sheet 28 to a relatively high, substantially uniform potential. As drum 30 rotates master sheet 28 in the direction of arrow 34, the charge bleeds away from the master sheet, except in the image areas and test area. Next, developer rolls 36 and 38 advance yellow liquid developer material into contact with master sheet 28. The yellow liquid developer includes a clear carrier and yellow colored toner. In this way, liquid developer material is brought into contact with the image areas and test area formed on the master sheet. Developer material is attracted electrostatically to the image areas and test area forming a yellow liquid image and a yellow liquid test area on master sheet 28. Preferably, the developer material includes a clear liquid insulating carrier having pigmented particles, i.e. toner particles, dispersed therein. A suitable clear insulating liquid carrier may be made from an aliphatic hydrocarbon, such as an Isopar, which is a trademark of the Exxon Corporation, having a low boiling point. The toner particles include a pigment associated with a polymer. An example of a suitable liquid developer material is described in U.S. Pat. No. 4,582,774, issued to Landa in 1986, the relevant portions thereof being incorporated into the present application. Metering roll 40 controls the quantity of developer material deposited on master sheet 28 and removes the excess therefrom. The master sheet having the test area thereon developed with yellow liquid developer material passes beneath a densitometer, indicated generally by the reference numeral 51. Densitometer 51 is positioned adjacent master sheet 28 to generate electrical signal proportional to the developed liquid on the test area. The detailed structure of densitometer 51 will be described hereinafter with reference to FIGS. 3 through 6, inclusive.

After the image areas and test area on master sheet 28 are developed, drum 30 rotates the developed liquid image to the transfer station. Copy sheet 18 is advanced to the transfer station in synchronism with the developed liquid image on master sheet 28. The transfer station has an electrically biased roll 42 and corona generator 44. Sheet 18 is interposed between master sheet 28 and roll 42. Thereafter, transport 24 interposes sheet 18 between corona generator 44 and master sheet 28. Roll 42 is electrically biased to a suitable magnitude and polarity to tack sheet 18 to master sheet 28. Corona generator 44 sprays ions onto the backside of sheet 18 to attract the developed liquid image from master sheet 28 thereto. After the developed image has been transferred to sheet 18, the master sheet passes through the next cycle, i.e. a cleaning cycle, and sheet 18 advances to the next printing module. During the first cycle, corona generator 46 and cleaning roll 48 are non-operative. In contradistinction, corona generator 46 and cleaning roll 48 are operative during this cleaning cycle with corona generators 32 and 44, developer rolls 36 and 38, and metering roll 40 and densitometer 51 being non-operative. Corona generator 46 sprays ions onto master sheet 28 to neutralize the charge thereon. Cleaning roller 48 scrubs the surface of master sheet 28 clean. To assist in this action, liquid carrier may be fed onto the surface of cleaning roller 48. Preferably, the cleaning fluid is the carrier of the liquid developer material, i.e. a clear low boiling point aliphatic hydrocarbon, such as an Isopar, which is a trademark of the Exxon Corporation.

Figure 3:
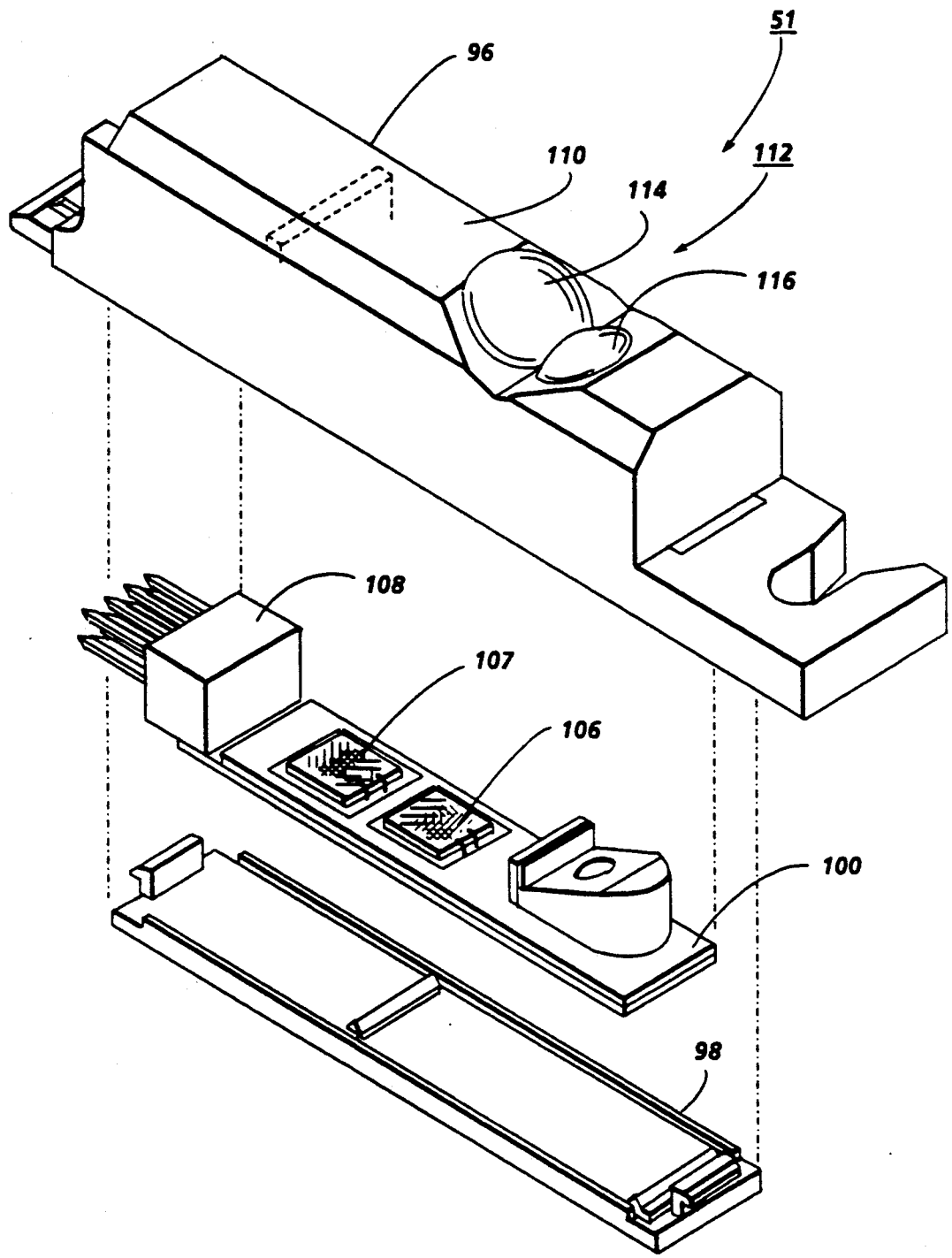
FIG. 3 is a schematic perspective view showing the densitometer used in the FIG. 2 printing module.
Figure 4:
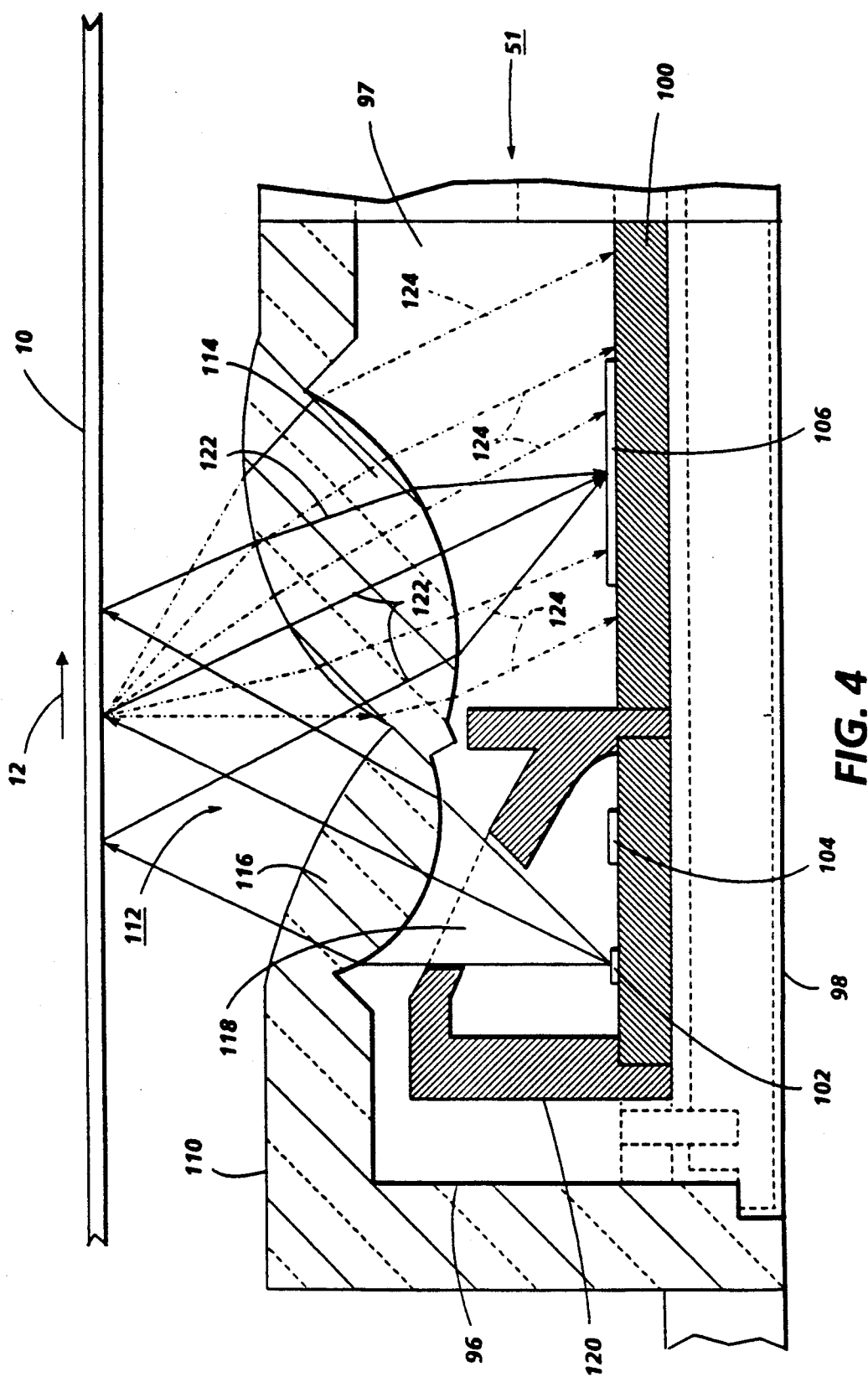
FIG. 4 is a fragmentary, sectional elevational view of the FIG. 3 densitometer.

Referring now to FIGS. 3 and 4, densitometer 51 is shown thereat in greater detail. Densitometer 51 includes a generally rectangularly shaped molded housing 96 made preferably from an acrylic material or any other suitable optically transparent material. Housing 96 defines a chamber 97. A cover 98 encloses the bottom of housing 96. A printed circuit wiring board 100 is mounted between cover 98 and housing 96 in chamber 97. Printed circuit board 100 supports a suitable light emitting diode (LED) 102 for providing light rays to illuminate the test area having liquid developer material thereon. A control photodiode 104 and a photodiode array 106 are also mounted on printed circuit board 100. The details of photodiode array 106 will be described hereinafter with reference to FIG. 5. Connector 108 is also mounted on printed circuit board 100. An integrated circuit chip, indicated generally by the reference numeral 107, is electrically connected to LED 102, photodiode 104 and photodiode array 106 to provide drive current to LED 102 and to process the signals from photodiode 104 and photodiode array 106. The top surface 110 of housing 96 defines a V-shaped recess, generally indicated by the reference numeral 112. One surface of the V-shaped recess 112 supports a condenser lens 116 which is an integral collimating lens. The other surface of the V-shaped recess 112 supports another condenser lens 114 which is an integral collector lens. LED 102 generates light rays which are transmitted through an aperture 118 in cavity 120 onto condenser lens 116. The light rays generated by LED 102 are in the visible spectrum ranging from about 4000 Angstrom to about 7000 Angstroms. Preferably, a red LED is used. A red LED emits lights rays in the visible spectrum from about 5800 Angstroms to about 7000 Angstrom. The color toner particles used in the liquid developer material substantially scatters light rays in the visible spectrum. Condenser lens 116 collimates the light rays and focuses the light rays onto the test area having the liquid developer material thereon. Photodiode 104 is positioned to receive a portion of the LED radiant flux reflected from the walls of cavity 120. The output signal from photodiode 104 is compared with a reference signal and the resultant error signal used to regulate the input current to LED 102 to compensate for LED aging and thermal effects. The light rays reflected from the surface of the test area having the liquid developer material deposited thereon are collected by condenser lens 114 and directed onto the surface of photodiode array 106. The specular component of the reflected light rays or flux, as shown by arrows 122, is focused on a small spot on surface of the central segment of photodiode array 106. The diffuse components of the reflected light rays or flux, as shown by arrows 124, flood the entire surface of photodiode array 106. Further details of the structure of the densitometer may be found in Co-pending U.S. patent application Ser. No. 07/246,242, filed in Sept. 19, 1988 by Hubble III et al., the relevant portions thereof being hereby incorporated into the present application. However, the densitometer described therein projects infrared light rays and is adapted for use with a dry developer material.

Figure 5:
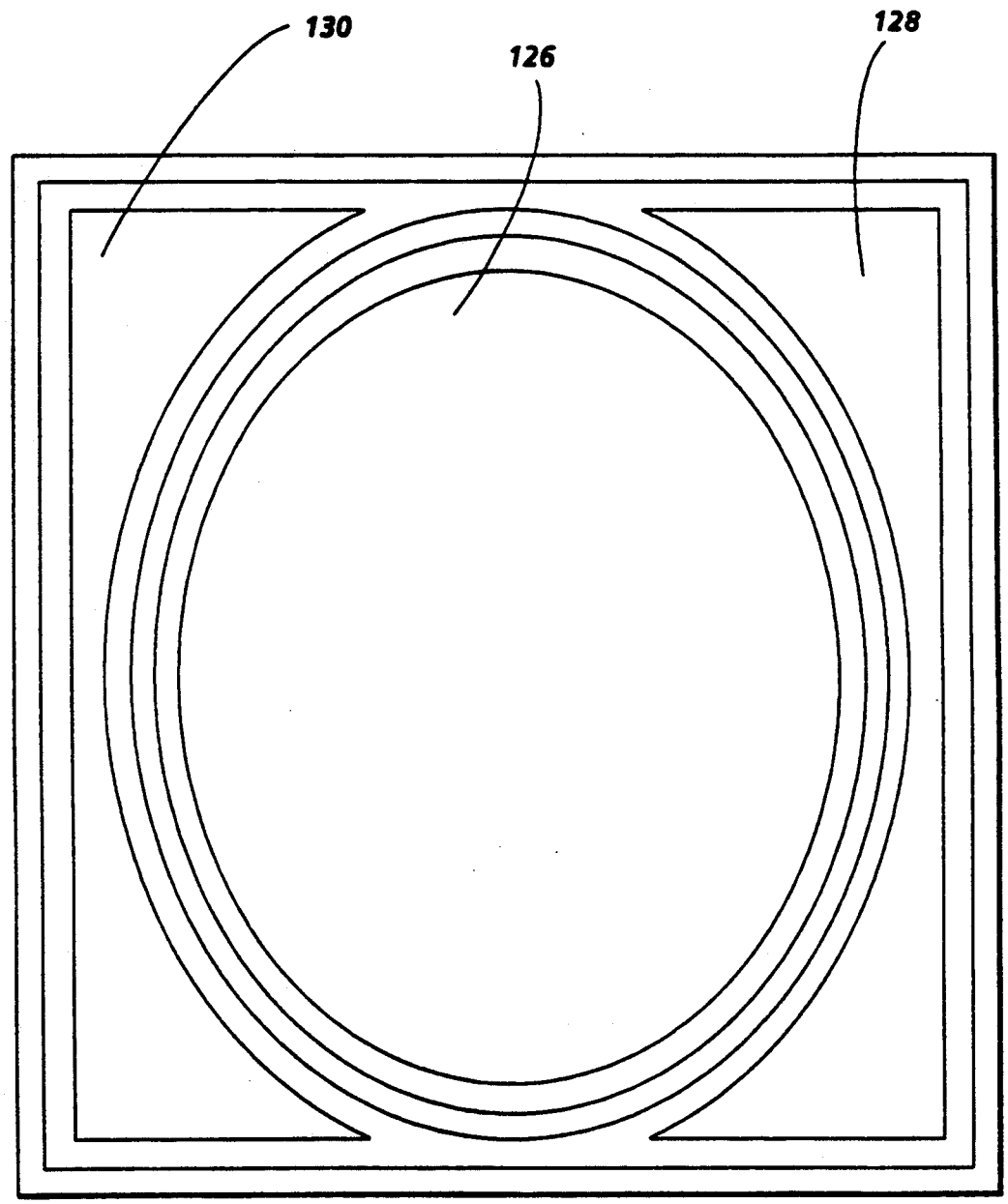
FIG. 5 is an enlarged plan view of the photodiode array used in the FIG. 3 densitometer.

Turning now to FIG. 5, there is shown photodiode array 106 in greater detail. Preferably, photodiode 106 is about 5 millimeter square. Photodiode array 106 receives the light rays transmitted through condenser lens 116. These light rays are reflected from the surface of the master sheet having the test area with the liquid developer material thereon. A central photodiode 126 receives a portion of the total reflected light rays or flux. The total reflected light rays or flux includes the specular component and the diffuse component of the reflected light rays or flux. Thus, central photodiode 126 generates an electrical signal proportional to the total reflected flux including the diffuse component and the specular component thereof. As shown, central photodiode 126 is preferably substantially elliptical. Edge photodiodes 128 and 130 are configured to compliment central photodiode 126 to complete photodiode array 106 which is substantially square in shape. Edge photodiodes 128 and 130 are substantially identical to one another, being shaped as mirror images of one another. Edge photodiodes 128 and 130 are positioned to receive only the diffuse component of the reflected light rays or flux transmitted through condenser lens 116. Hence, the electrical signal generated by edge photodiodes 128 and 130 is proportional to only the diffuse component of the reflected light rays or flux. Subtraction of the combined electrical signals of the edge photodiodes from the electrical signal from the central photodiode yields a resultant electrical signal proportional to the reduction in the specular component of the light rays or flux reflected from the surface of master sheet 28 having the test area with the liquid developer material thereon. A block diagram reflecting the integrated circuit 107 used to measure the specular component of the light rays is shown in FIG. 6.

Figure 6:
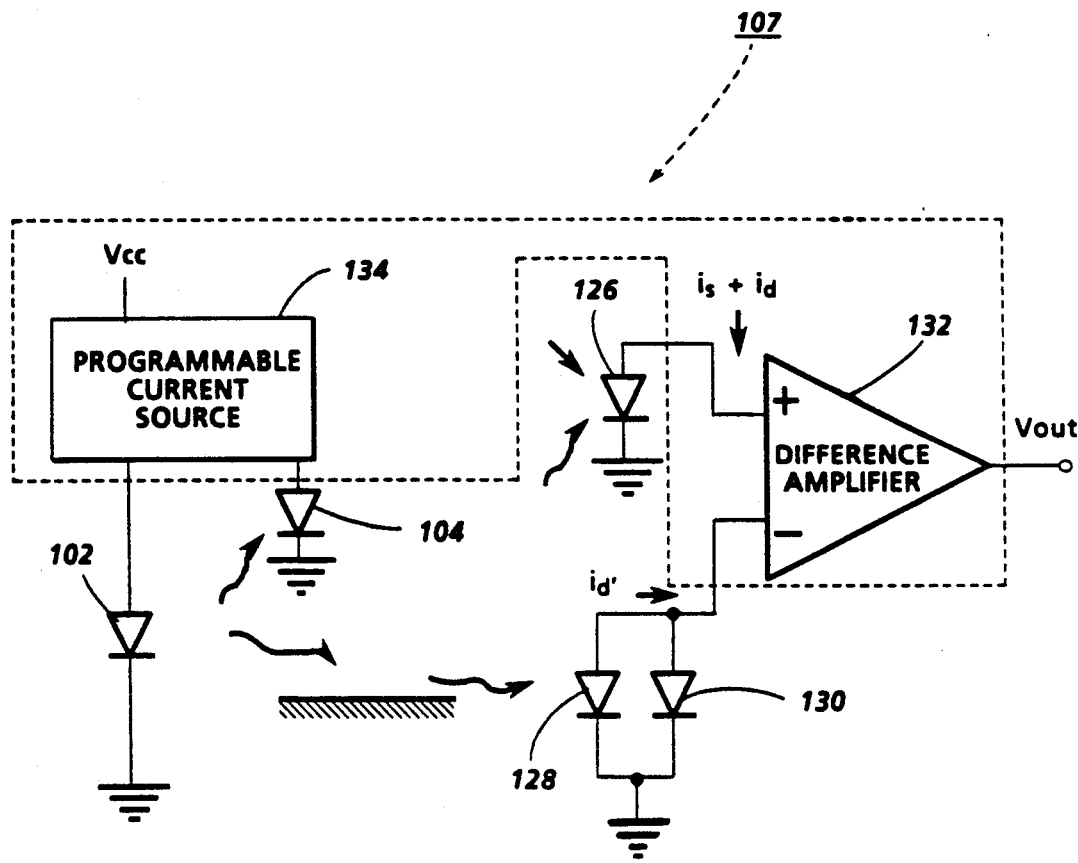
FIG. 6 is a block diagram of the control logic associated with the FIG. 3 densitometer.

As shown in FIG. 6, central photodiode 126 generates an electrical signal proportional to the the sum of the specular and diffuse components of the light rays. Central photodiode 126 is electrically connected to difference amplifier 132. The electrical output signals from photodiodes 128 and 130 are proportional to the diffuse component of the light rays. Photodiodes 128 and 130 are electrically connected to difference amplifier 132. The electrical signals from photodiodes 128 and 130 are combined and transmitted to difference amplifier 132. The voltage output, $V_{out}$, from difference amplifier 132 may be expressed as:

$$V_{out} = G_1(i_s + i_d) - G_2(i_{d'})$$

where:

$G_1$ and $G_2$ are gains of difference amplifier 132;

$i_s$ is the specular component of the current output from central photodiode 126;

$i_d$ is the diffuse component of the current output from central photodiode 126; and $i_{d'}$ is the diffuse components of the combined current output from edge photodiodes 128 and 130.

$G_1$ and $G_2$ are set such that $$G_1(i_d) = G_2(i_{d'}).$$

This yields $$V_{out} = G_1(i_s).$$

Thus, the voltage output form difference amplifier 132 is proportional only to the specular component of the photodiode current output. This voltage output provides a measure of the area coverage of colored liquid developer material deposited on the test area formed on the master sheet. When 100% of the test area is developed with liquid developer material, the specular reflectivity is zero and the output from difference amplifier 132 will be zero. When the test area is undeveloped, i.e. 0% of the test area is developed with liquid developer material, the output will correspond to the specular reflectivity of the master sheet, i.e. a non-zero value.

With continued reference to FIG. 6, the electrical signal from control photodiode 104 is transmitted through suitable circuitry to generate a voltage output which regulates a current source 134. The current source energizes LED 102. In this way, a feedback loop is formed for driving LED 102 to provide a relatively constant output. Thus, if the signal from photodiode 104 changes, the output from current source 134 is suitably adjusted to maintain a relatively constant light output from the LED 102.

In recapitulation, the densitometer illuminates a portion of a master sheet having a liquid developer material deposited on a test area. The light rays emitted from the densitometer are in the visible spectrum range. The densitometer detects the total and diffuse components of the reflectivity of the light rays. The difference is obtained and a signal generated proportional to the specular component of the reflectivity of the light rays generated. In this way, the densitometer is capable of sensing the presence or absence of liquid developer on a master sheet.

It is, therefore, evident that there has been provided in accordance with the present invention, a densitometer that fully satisfies the aims and advantages hereinbefore set forth. While this invention has been described in conjunction with a specific embodiment thereof, it is evident that many alternatives, modifications and variations will be apparent to those skilled in the art. Accordingly, it is intended to embrace all such alternatives, modifications and variations as fall within the spirit and broad scope of the appended claims.

We claim:

1. An apparatus for measuring the reduction in the specular reflectance of a surface having a liquid deposited on a portion thereof, including:
   means for projecting light rays, in the visible spectrum, onto the the portion of the surface having the liquid thereon;
   a first condenser lens interposed between said projecting means and the portion of the surface having the liquid deposited thereon so that collimated light rays are projected thereon;
   means for detecting the total reflectivity of the portion of the surface having the liquid deposited thereon and the diffuse component of the total reflectivity of the portion of the surface having the liquid deposited thereon and generating a total signal indicative of the total reflectivity and a diffuse signal indicative of the diffuse component of the total reflectivity, said detecting means comprises a photosensor array,
   a second condenser lens interposed between said detecting means and the surface having the liquid deposited for receiving the light rays reflected therefrom, said photosensor array comprises a central photosensor positioned to receive the total light rays transmitted through said second condenser lens, and at least one edge photosensor positioned about the periphery of said central photosensor to receive the diffuse component of the light rays transmitted through said second condenser lens; and
   means, responsive to the difference between the total signal and the diffuse signal, for generating a specular signal indicative of the specular component of the total reflectivity.

2. An apparatus according to claim 1, wherein said projecting means includes a light emitting diode.

3. An apparatus according to claim 2, wherein:
   said central photosensor includes a central photodiode; and
   said edge photosensor includes an edge photodiode.

4. An apparatus according to claim 1, further including means for measuring and controlling the intensity of the light rays being emitted from said projecting means.

5. An apparatus according to claim 4, wherein said measuring and control means includes a control photosensor positioned adjacent said projecting means to detect the variation in intensity of the light rays being emitted from said projecting means.

6. A printing machine of the type in which the reduction in specular reflectance of a member having a liquid deposited on a portion thereof is detected, wherein the improvement includes:
   means for projecting light rays, in the visible spectrum, onto the portion of the member having the liquid deposited thereon;
   a first condenser lens interposed between said projecting means and the portion of the member having the liquid deposited thereon so that collimated light rays are projected thereon;
   means for detecting the total reflectivity of the portion of the member having the liquid deposited thereon and the diffuse component of the total reflectivity of the portion of the member having the liquid deposited thereon and generating a total signal proportional to the total reflectivity and a diffuse signal proportional to the diffuse component of the total reflectivity of the liquid, said detecting means includes a photosensor array;
   a second condenser lens interposed between said detecting means and the member having the liquid deposited thereon for receiving the light rays reflected therefrom, said photosensor array comprises a central photosensor positioned to receive the total light rays transmitted through said second condenser lens, and at least one edge photosensor positioned about the periphery of said central photosensor to receive the diffuse component of the light rays transmitted through said second condenser lens; and
   means, responsive to the difference between the total signal and the diffuse signal, for generating a specular signal proportional to the specular component of the total reflectivity.

7. A printing machine according to claim 6, wherein said projecting means includes a light emitting diode.

8. A printing machine according to claim 7, wherein:
   said central photosensor includes a central photodiode; and
   said edge photosensor includes an edge photodiode.

9. A printing machine according to claim 6, further including means for measuring and controlling the intensity of the light rays being emitted from said projecting means.

10. A printing machine according to claim 9, wherein said measuring and control means includes a control photosensor positioned adjacent said projecting means to detect the variation in intensity of the light rays being emitted from said projecting means.

11. A densitometer adapted to measure the reduction in the specular component of the reflectivity of a surface having a liquid deposited on a portion thereof, including
   a collimating lens;
   a light source positioned to project light rays, in the visible spectrum, through said collimating lens onto the portion of the surface having the liquid deposited thereon;
   a collector lens positioned to receive the light rays reflected from the portion of the surface having the liquid deposited thereon;
   a photosensor array positioned to receive the light rays transmitted through said collector lens and generating a total signal proportional to the total reflectivity of the portion of the surface having the liquid deposited thereon and a diffuse signal proportional to the diffuse component of the total reflectivity of the portion of the surface having the liquid deposited thereon; and control circuitry, electrically connected to said photosensor array, for comparing the total signal and the diffuse signal to determine the difference therebetween for generating a specular signal proportional to the specular component of the total reflectivity of the surface having the liquid deposited thereon.

12. A densitometer according to claim 11, wherein said light source projects light rays having a spectrum ranging from about 4000 Angstrom to about 7000 Angstrom.

13. A densitometer according to claim 12, wherein said light source projects light rays having a spectrum ranging preferably from about 5800 Angstrom to about 7000 Angstrom.

14. A densitometer according to claim 11, wherein said photosensor array includes:
   a central photosensor positioned to receive the total light rays transmitted through said collector lens; and
   at least one edge photosensor positioned about the periphery of said central photosensor to receive the diffuse component of the light rays transmitted through said collector lens.

15. A densitometer according to claim 14, wherein said light source includes a light emitting diode.

16. A densitometer according to claim 15, wherein:
   said central photosensor includes a central photodiode; and
   said edge photosensor includes an edge photodiode.

17. A densitometer according to claim 16, further including means for measuring and controlling the intensity of the light rays being emitted from said light source.

18. A densitometer according to claim 17, wherein said measuring and controlling means includes a control photosensor positioned adjacent said light source to detect the variation in intensity of the light rays being emitted from said light source.

* * * * *